(12) United States Patent
MacDonald et al.

(10) Patent No.: US 6,485,543 B1
(45) Date of Patent: Nov. 26, 2002

(54) GAS CHROMATOGRAPHY OVEN HEATERS

(75) Inventors: Stephen J. MacDonald, 17 Norwood Rd., P.O. Box 1472, Salem, NH (US) 03079; Peter Germano, Northborough, MA (US); Edwin Jahngen, Kingston, NH (US)

(73) Assignee: Stephen J. MacDonald, Salem, NH (US)

( * ) Notice: Subject to any disclaimer, the term of this patent is extended or adjusted under 35 U.S.C. 154(b) by 1 day.

(21) Appl. No.: 09/663,425

(22) Filed: Sep. 16, 2000

(51) Int. Cl.[7] .............................................. B01D 15/08
(52) U.S. Cl. ........................................... 95/87; 96/102
(58) Field of Search .................. 95/82–87; 96/101–105, 96/107

(56) References Cited

U.S. PATENT DOCUMENTS

| | | | | |
|---|---|---|---|---|
| 3,305,000 A | * | 2/1967 | Bullen et al. .............. 96/102 X |
| 3,422,603 A | * | 1/1969 | Redmond, Jr. ............... 96/103 |
| 4,070,169 A | * | 1/1978 | Iwao et al. .................... 96/101 |
| 4,088,458 A | * | 5/1978 | Jourdan ..................... 96/106 X |
| 4,599,169 A | * | 7/1986 | Ray .......................... 96/101 X |
| 4,771,628 A | * | 9/1988 | Sisti et al. ................ 96/101 X |
| 4,854,952 A | * | 8/1989 | Stepien ........................ 96/105 |
| 4,869,876 A | * | 9/1989 | Arfman et al. ........... 96/102 X |
| 5,634,961 A | * | 6/1997 | Gordon .................... 96/102 X |
| 5,744,029 A | * | 4/1998 | Li et al. ................... 96/101 X |
| 5,942,675 A | * | 8/1999 | Wilson ..................... 95/82 X |
| 6,126,728 A | * | 10/2000 | Walsh et al. .................. 96/101 |

* cited by examiner

*Primary Examiner*—Robert H. Spitzer

(57) ABSTRACT

A gas chromatography system with suspended tubular separation column(s) in an enclosed convection oven where a gas medium is heated by at least two electrically powered heaters. A kit to modify gas chromatographic ovens for operation with at least two electrically powered heaters. The heaters are positioned to promote even heating along the length of the column(s) and shielding of the column(s) from radiant heat. The heaters can provide faster heating rates at elevated temperatures.

16 Claims, 5 Drawing Sheets

GAS CHROMATOGRAPHY OVEN HEATERS

Disclosed herein are gas heaters for gas chromatography convection ovens, methods for applying such heaters in gas chromatography systems and gas chromatography systems having additional gas heaters for enhanced temperature programming performance.

BACKGROUND OF THE INVENTION

In gas chromatography the components of a mixture are separated as volatilized components and carried through a separation column to a detector. The separation column is typically a long capillary suspended in a convection oven. Many gas chromatographic applications require the oven to be heated in a programmed manner during the analysis.

FIG. 1 illustrates the space in a convection oven 1 useful in gas chromatography. The oven space is typically divided by a baffle 5 into a heater space 3 containing a heater element 6 and a fan 2, and a column space 4 containing one or more separation columns (not shown). The baffle typically has a central bore allowing air to be drawn into the fan from the column space into the heater space. The baffle is also designed to permit flow from the heater space to the column space between the baffle periphery and the walls of the oven to permit a circulating flow of forced hot gas, typically air. Electrical power is applied to a heater 6 (e.g. resistively heated metal wire) during the heating cycle from a power supply 9 connected to a source of electric power 10. A temperature control circuit 7 receives a signal indicative of the oven temperature from a sensor 8 and sends a control signal to a power supply 9.

It is sometimes desirable to minimize the time required to analyze a sample. The time required to analyze a sample by gas chromatography depends on many factors including the heating rate that the oven can achieve. The heating performance of a gas chromatographic oven is affected by (a) the power of a heater, (b) the characteristics of the heat transfer medium (typically air), (c) and the rate of heat loss to the surroundings. Electrical power is supplied to commercial gas chromatography from a single electrical power source, for example the power supply is connected to 100 volt (V), 20 amp or 220 V, 20 amp service. Therefore, the ability to generate heat energy is limited by the available electrical power. The heating power is limited by the amount of electrical current that can be conducted through the wire, which is limited by the electrical source, and the physical properties of the wire. Table 1 shows the heating performance of a typical gas chromatography.

TABLE 1

Typical Gas chromatographic selectable oven heating rates

| Temperature range (° C.) | Maximum Oven Heating Rate (° C./min) 120 Volt | Maximum Oven Heating Rate (° C./min) 220 Volt |
| --- | --- | --- |
| 50 to 70 | 75 | 120 |
| 70 to 115 | 45 | 120 |
| 115 to 175 | 40 | 110 |
| 175 to 300 | 30 | 80 |
| 300 to 450 | 20 | 65 |

A temperature heating profile for a gas chromatographic oven is illustrated in FIG. 2. The solid line represents the "true maximum heating rate" which is the heating rate for the oven when full power is applied to the heater. Because a controlled heating rate is usually desired, in practice the instrument is usually limited to selected heating rate values including a "maximum selectable heating rate" (as indicated by the dashed line) which is the maximum heating rate that can be selected for a particular gas chromatograph. As such, the maximum selectable heating rate is an artificial limit imposed by design.

Gas chromatograph ovens can operate at the maximum selectable heating rate over a limited temperature range, depending upon the allowed values and the heating performance of the oven. At low temperatures there is sufficient heating power available to overcome the heat loss to the surroundings and the true maximum heating rate exceeds the maximum selectable heating rate. Under these conditions the gas chromatograph oven can achieve the maximum selectable heating rate. As the temperature of the oven rises, however, the true maximum heating rate decreases such that the maximum selectable heating rate can no longer be achieved. This occurs at a temperature less than that represented by the intersection of the two lines shown in FIG. 2. The gas chromatographic oven cannot achieve the maximum selectable heating rate above the upper performance temperature. This condition results in uncontrolled operation of the gas chromatograph. Results obtained under such conditions are less reliable compared to results obtained under controlled heating conditions. Accordingly, the heating rate is often reduced below the maximum selectable heating rate when the oven is heated above the upper performance temperature.

Gas chromatographs having temperature-programmable ovens have been commercially available for more that 30 years. Temperature programming of gas chromatography systems is important for facilitating the separation of mixtures of components. Unique heater systems for gas chromatography systems are known in the art. See, for instance, U.S. Pat. Nos. 3,043,127; 3,057,183; 3,165,146; 3,225,520; 3,581,465; 4,050,911; 4,923,486; 5,028,243; 5,215,556; 5,544,276; 5,547,497; 5,744,029; 5,807,426; 5,830,353, all of which are incorporated herein by reference in their entireties.

Despite the great variation in heating systems, modern gas chromatography apparatus is deficient in its ability to maintain high programmed rates of heating over an extended temperature range, e.g. 70° C. per minute at temperatures much over 115° C. when supplied with 110 volt 20 amp service.

The desire to achieve faster heating rates is evidenced by design improvements witnessed throughout their development. Attempts to improve their heating performance include reducing the thermal mass associated with gas chromatographic ovens thereby reducing the power required to heat the oven and the heat loss to the surroundings. The heating performance of the oven heater has been improved. Circulation of the heat exchange medium has been improved by the proper placement of fans and the design of baffles. Some gas chromatographs (Model 222 Perkin-Elmer Corp., Norwalk, Conn. USA) also employed resistively heated metal tubes containing a separation medium to achieve better heating performance.

More recently, faster heating has been achieved by passing an electrical current through an electrically conductive coating on the outside of the separation column (Jain, V. and Phillips, J. (1995); J. Chrom. Sci.33:55.). Another technique employs resistively heated wires wrapped around the separation column (Ehrmann, E. et. al. (1996); J. Chrom. Sci. 34:533). A commercial instrument (Flash GC, Thermedics Detection Inc. Chelmsford, Mass.) uses electrical current to heat a low thermal mass metal sheath containing a separation column.

Modification kits have also become commercially available that permit faster heating of the separation column in existing gas chromatographs. An oven insert kit (PN G2646A, Agilent Technologies, Wilmington, Del. USA) is comprised of an insulating pillow that is inserted into the column space to reduce the volume of the oven. A kit in which the separation column is located within a thin metal sheath that can be rapidly heated is also available (EZ Flash GC accessory, Orion Research, Beverly, Mass. USA).

An object of this invention is to provide improvements in the heating performance of gas chromatography systems to permit high heat rates of thermal programming at elevated temperatures.

SUMMARY OF THE INVENTION

This invention provides gas chromatography systems with improved temperature programming capability due to the addition of at least one additional electrically powered gas heater. Such heaters can be provided in a kit comprising means for mounting the heater in a convection oven to promote even distribution of convective heat from the heater to the separation column. The means for mounting the heater preferably also comprises a radiant heat shield between said heaters and separation columns.

BRIEF DESCRIPTION OF THE DRAWINGS

FIGS. 34 and 3B illustrate different views of a heater element.

DETAILED DESCRIPTION OF PREFERRED EMBODIMENTS

As used herein "true maximum heating rate" means the maximum heating rate that an oven can achieve when full power is applied to the heater(s).

As used herein a "maximum selectable heating rate" means the maximum heating rate that can be selected for a particular gas chromatograph oven.

As used herein "maximum performance temperature" means the temperature that defines the upper limit at which the gas chromatographic oven can heat at the maximum selectable heating rate.

As used herein "temperature regulation" means control of oven temperature by means of a feedback control circuit or a simple "on-off" condition switch that activates a heater to follow a preset heating profile.

As used herein "heating performance" means the ability of a gas chromatograph oven to increase temperature over time.

As used herein "even heating" refers to a thermal condition in a gas chromatograph oven where there is a minimal thermal gradient along the length of the separation column.

As used herein "power supply" means a component of a gas chromatograph that applies electrical power from an electrical power source to a gas heater under direction from a temperature control circuit.

As used herein "temperature control circuit" means a circuit that receives a signal indicative of the oven temperature and sends a signal indicative of the power required to achieve a preset temperature, e.g. a temperature program, to a power supply.

As used herein "electrical power source" means electrical service available to the gas chromatograph, e.g. 120 V 20 amp or 220 V 20 amp service.

In a significant departure from the prior art, the present invention will be understood to overcome the limitations of gas chromatographic ovens that employ one gas heater in a convection oven to heat the separation column. Further, it will be understood that the present invention can be used as an integral part of the design of a gas chromatographic oven or as a modification to existing gas chromatographic ovens.

Figure 1:
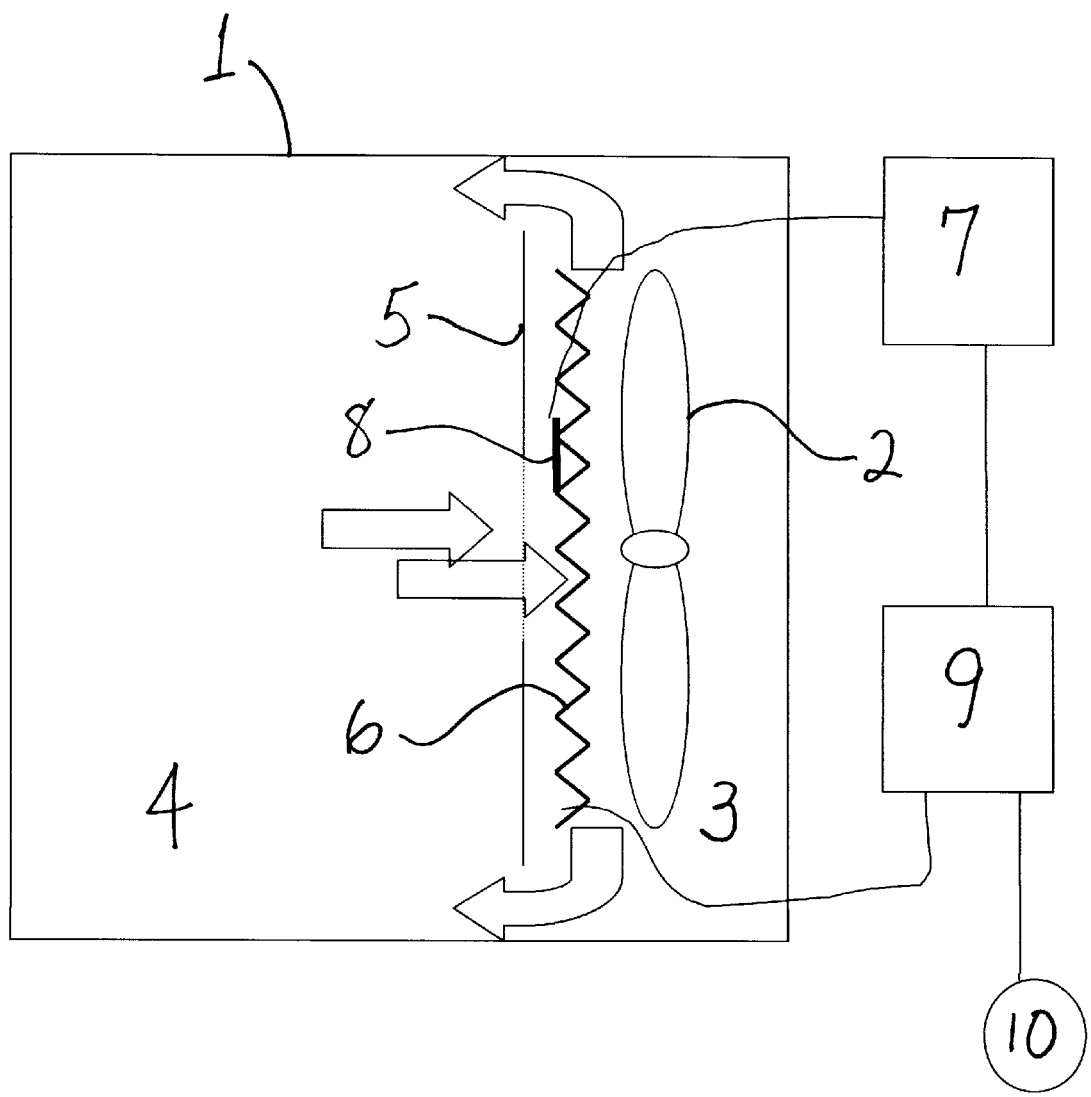
FIG. 1 is a schematic illustration of typical gas chromatography convection oven system.
Figure 2:
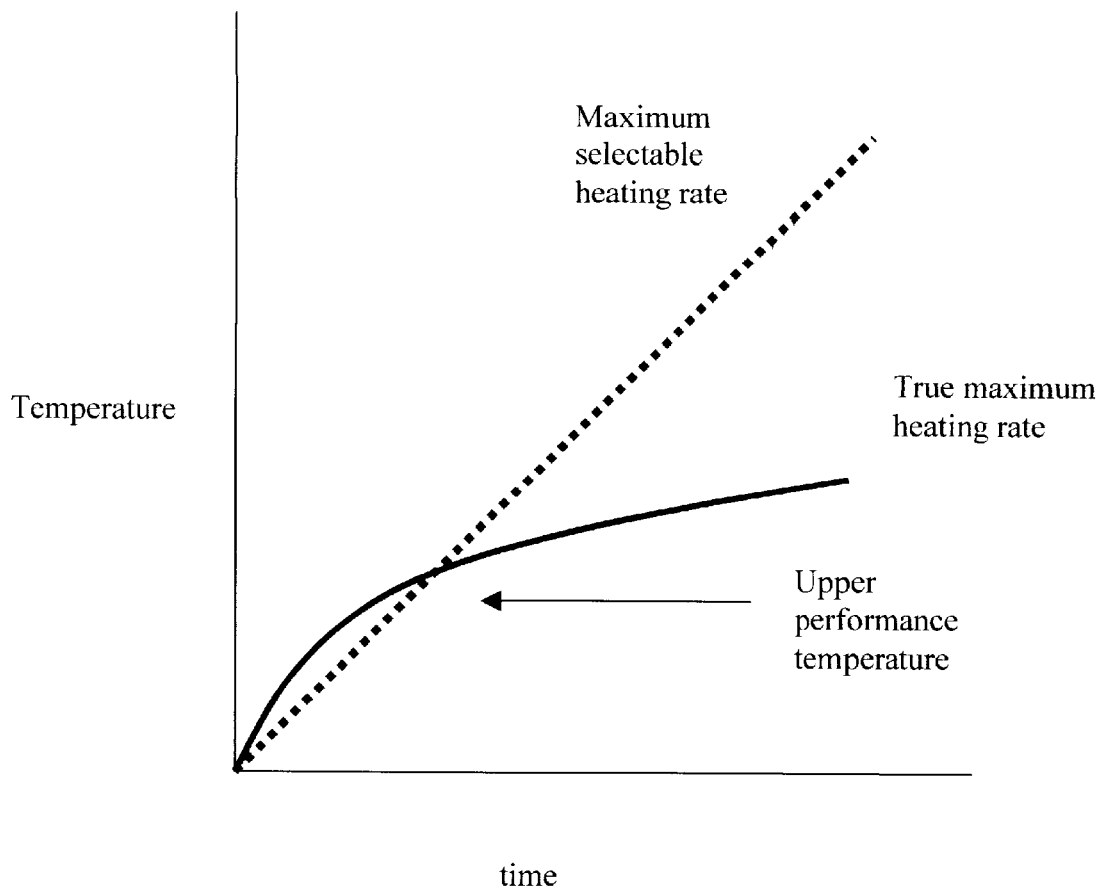
FIG. 2 is a graphical illustration of a temperature programming profile for a gas chromatography system.
Figure 3A:
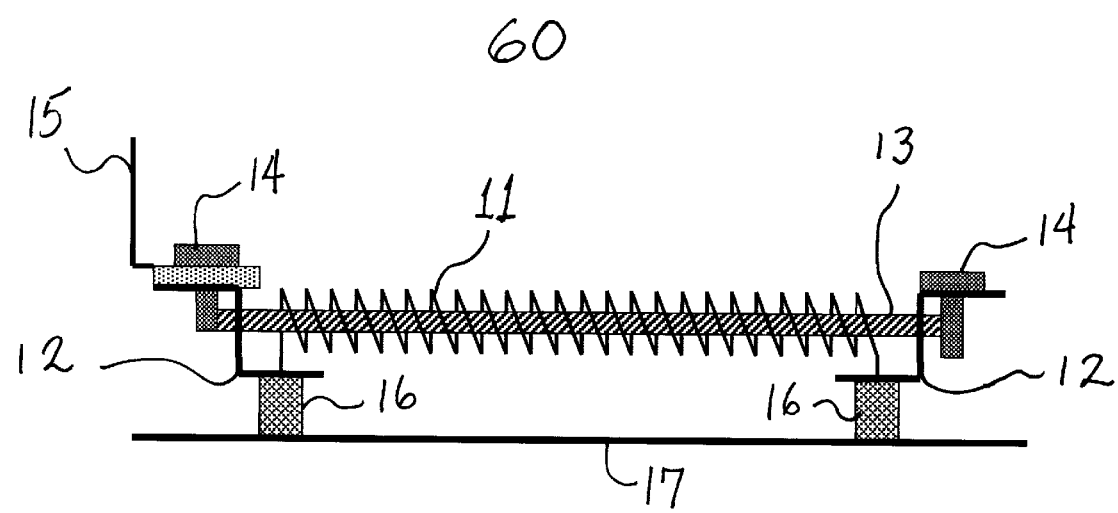
Figure 3B:
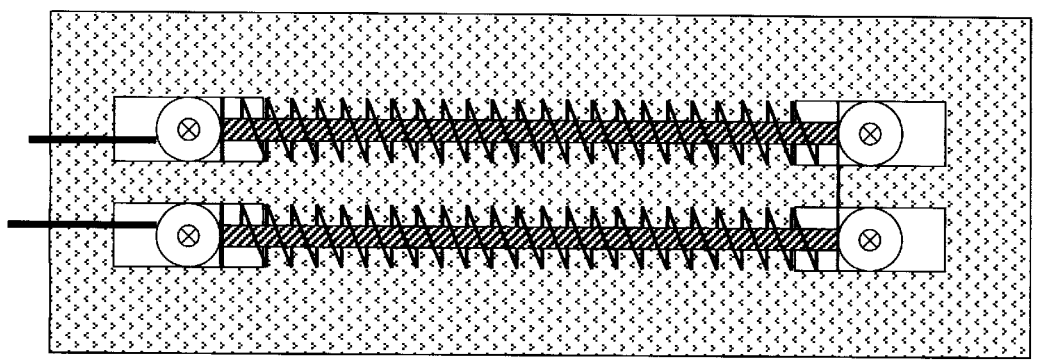

The heating elements in the heaters of this invention are most conveniently made from any electrically resistive heating wire, e.g. a nickel chromium alloy. The length and diameter of the wire will depend on the resistance, available power and desired heat output. Although resistive heating heater wire design is a common skill in the art, a useful starting point is a nickel chromium alloy wire about 14 feet (about 4.2 meters) long and 0.032 inches (0.8 millimeters) in diameter, which will provide a resistance of about 8 to 11 ohms at 20° C. With reference to FIGS. 3A and 3B there is shown an electrically powered gas heater 60 for use in this invention. A resistive heating wire 11 is anchored at each end by electrically conductive support brackets 12, e.g. a metal such as stainless steel. The wire is supported along its length by an insulating rod 13, e.g. glass, which itself is supported by the support brackets. Alternatively, the wire may be self-supporting. The rod is kept in place by fasteners 14 that may also act to secure electrical wire leads 15. The support brackets are mounted on insulating standoffs 16, e.g. ceranmic, which are mounted to a support plate 17, which can also serve as a radiant heat shield. The support plate must be high temperature resistant and can be a metal or refractory material. A useful material is stainless steel. Although the size of the support plate will vary depending on intended location and oven dimensions, a useful size plate is 3 inch×11 inch×0.035 inch (75 mm×280 mm×0.8 mm).

One aspect of this invention provides a kit for improving the heating performance of a gas chromatograph oven having a separation column suspended in a gas medium heated by an electrically powered heater. A kit of this invention comprises at least one electrically powered gas heater. It may also comprise a radiant heat shield. The heater is preferably supplied mounted on a bracket for mounting in an oven. The kit can optionally also comprise a power supply for the heater. In certain embodiments the kit can also comprise a temperature control circuit for regulating power supplies for all heaters.

Figure 4:
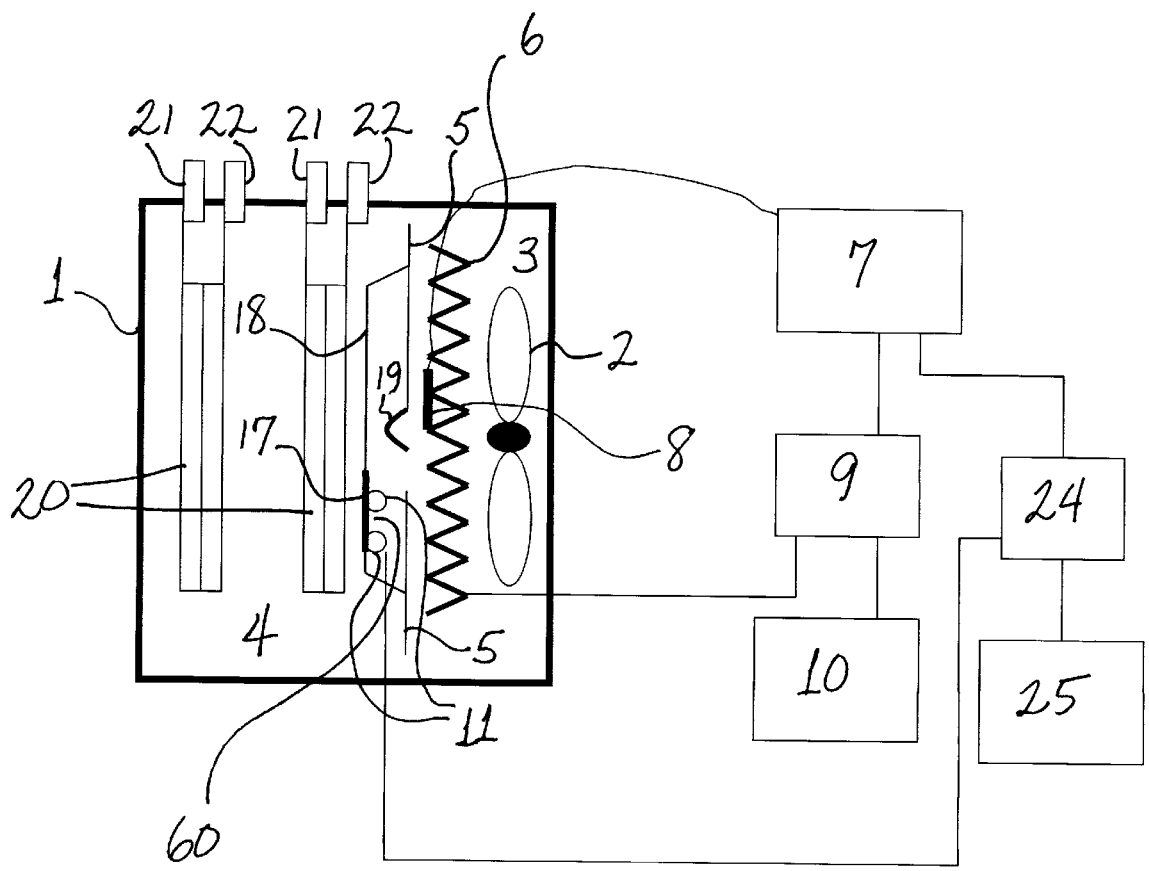
FIGS. 4 and 5 illustrate convection ovens according to this invention.

With reference to FIG. 4 there is shown a gas chromatograph oven 1 with separation columns 20, each connected to an injector 21 and detector 22. The oven is heated by an original heater 6, typically comprising a metal wire capable of heating the oven at a maximum selectable heating rate to an upper performance temperature. Heated air is circulated by fan 2 around the baffle to heat the column space 4. An additional heater 60 is mounted in space 4 by bracket(s) 18, e.g. one or more stainless steel rods. The bracket(s) can be fastened to the baffle or can clip over the top of the baffle and extend down to support the heater by connecting to plate 17. As shown, plate 17 can be mounted vertically adjacent to the baffle 5 in the lower part of space 4. The plate 17 blocks radiant heat from affecting the column(s) 20. In a simple form the kit can comprise a heater wire 11 mounted on a plate 17, together with a bracket 18. The plate serves to shield the column from radiant heat and direct heat flow. In other embodiments the plate 17 may be of a different shape, e.g. a U-shaped or circular shape, to promote even heat distribution along the length of the separation column. In other embodiments, the heater 60 may be positioned to direct heat to the circulation stream as it leaves space 3. In still other embodiments more than one heater may be located in space 3, e.g. adjacent to heater 6. In other embodiments a heater for improving the heating performance of a gas chromatograph oven may be located external to the oven 1.

Positioning heater 60 in column space 4 such that heat is directed into the air stream directed toward space 3 promotes even heating because fan 2 mixes the heat energy with the heat energy generated by the heater in compartment 3 and directs the mixed heat energy to the column space 4. Alternatively, the heater can be positioned to promote the direction of heat energy to the circulating air as it enters space 4. Other arrangements include a heater mounted around the center portion of the baffle 5 in space 4.

The bracket is formed to position the heater 60 to permit the heat generated to rise into the circulation stream created by fan 2. Heat is mixed with the heat generated by heater 6 and distributed into the column space 4. A shield 19, e.g. a 9 mm square piece of aluminum foil, is used to shield the temperature sensor from the radiant heat of the heater 60. Alternatively, the temperature sensor could be repositioned to avoid the radiant heat, e.g. on the column space side of plate 17.

Temperature control circuit 7, connected to sensor 8, regulates power supplies 9 and 24, which supply electrical service 10 and 25, respectively, to heaters 6 and 60 respectively. In a preferred embodiment, using more than one heater significantly increases the amount of heat energy that can be generated. Furthermore, connecting additional heaters to dedicated power supplies and electrical power sources permits the production of additional heat energy at moderate current levels. Operating the system at moderate currents reduces the need for high performance components for the gas chromatograph and high current sources of electrical power. Regulating each oven heater with a single temperature control circuit ensures similar heat contribution by each heater and eliminates the possibility of "cross-talk", i.e. where the heat output of one heater affects the heat output of another heater, resulting in an unbalanced operation of heaters. Other embodiments using at least two gas heaters with at least one power supply and at least one electrical source are made apparent by the disclosure of this invention. In other embodiments the kit can include a power supply 24 and cables for connecting the power supply to the heater, temperature control circuit, and electrical power source 25. Because of the enhanced heating performance achievable by this invention, it may be convenient to provide a temperature control circuit programmed for higher maximum heating rates and upper performance temperatures.

Figure 5:
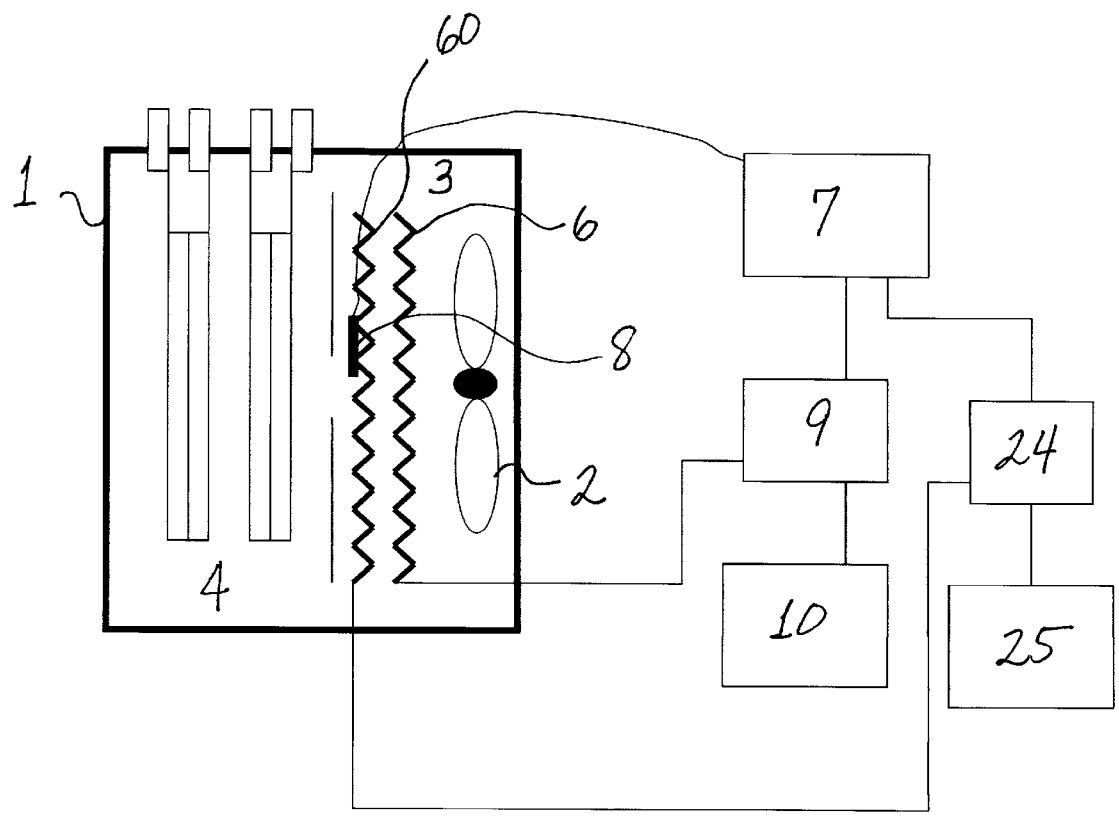

Another embodiment of the invention provides a gas chromatograph oven comprising two or more gas heaters as shown in FIG. 5. Two heaters 6 and 60 are located in space 3 of an oven 1. Where heater 6 comprises a coiled wire mounted in a circular configuration to baffle 5, heater 60 can also be mounted to baffle 5 in a circular configuration adjacent to heater 6. A single temperature control circuit 7 connected to sensor 8 regulates power supplies 9 and 24, which apply electrical power from electrical service 10 and 25, respectively, to heaters 6 and 60, respectively.

Additional embodiments of the invention include the use of different types of heating wires and different types of heaters such as high intensity lamps. Multiple heaters could also be arranged concentrically within the same plane in compartment 3 or in front of and behind the circulation fan 2. It is possible to position a heater in the column space 4 and provide sufficient shielding such that the radiant heat would not impact the separation column. If a heater is positioned in space 4 it should be arranged to promote even distribution of heat throughout the oven.

Another embodiment of the invention comprises a set of heaters in which at least one heater is a "smart" heater controlled by a temperature feedback circuit while additional heaters are merely turned on and off and follow a preset heating profile. The smart heater(s) responds to the temperature of the gas chromatograph oven and compensates accordingly to achieve the desired heating rate in the presence of heat contributed by other heaters.

Another embodiment of the invention comprises a multiple heater system having more than one temperature sensor and temperature controlling circuit.

Another embodiment of the invention comprises a system in which more than one heater is connected to the same power supply.

Another embodiment of the invention comprises a system with more than one heater located in a compartment external to a gas chromatograph oven 1, e.g. a separate oven in which a fluid, e.g. air, can be heated and mixed with the air in the gas chromatograph oven 1.

While the invention has been described and illustrated with reference to specific embodiments, those skilled in the art will recognize that modifications and variations may be made without departing from the principles of the invention as described herein above and set forth in the following claims.

What is claimed is:

1. A method for improving the heating performance of a gad chromatography system having a separation column suspended in a gas medium in an enclodes convection oven wherein the gas medium is heated by a first electrically-powered gas heater in response to a temperature controller, said method comprisisng adding at least one second electrically-powered gas heater to said covection oven and means for mounting said heater wherein convective heat from said heater is directed to a circulating fan for distribution to said column and wherein said means provides shielding between said column and radiant heat from said heater.

2. A method according to claim 1 wherein each of said heaters is connected to an electrical power supply which applies electrical power in response to a signal from a common temperature controller.

3. A gas chromatography system comprising a tubular separation column suspended in a gas medium in enclosed convection oven wherein the gas medium is heated by at least two electrically-powered gas heaters and circulation in said oven by a fan, wherein each of said heater is mounted in said oven so that said column is shield from radiant heat transfer from said heaters.

4. A gas chromatography system according to claim 3 wherein convective heat from said heaters is drawn to said fan for distribution to said column.

5. A gas chromatography system according to claim 4 wherein each of said heaters is connected to an independent electrical power supply.

6. A gas chromatography system according to claim 5 wherein each of said power supplies is connected to an independent power line feed.

7. A gas chromatography system according to claim 6 whereim a common temperature controller regulated all of said heaters.

8. A gas chromatography system according to claim 6 wherein each of said heaters is regulated by an independent temperature controller.

9. A gas chromatography system according to claim 8 further comprising a temperature sensor providing input to said controller and wherein said sensor is shielded from radiant heat from said heaters.

10. A chromatography system according to claim 4 wherein all of said heaters a common power supply.

11. A kit for improving the performance of a gas chromatography system havig a separation column suspended in a gas medium in an enclosed convection oven wherein the gas medium is heated by a first electrically-powered gas heater in response to a temperature controller and convective heat is directed to said column by a circulating fan, said kit comprising at least one second electrically-powered gas heater for said convention oven and means for mounting said second heater in said oven such that convective heat from said second heater is directed to said column by said circulating fan and such that said column is shielded from radiant heat from said second heater.

12. A kit according to claim 11 further comprising a temperature controller for simultaneously regulating all of said heaters.

13. A kit according to claim 11 further comprising a second, independently-fed, electrical power supply for each of said second heaters.

14. A kit according to claim 13 further comprising a temperature controller for simultaneously regulating all of said heaters.

15. A kit according to claim 13 wherein each of said second power supplies is rated for up to 4000 watt service.

16. A kit according to claim 11 which provides a temperature rise rate for said oven of at least 70° C. per minute up to 250° C.

* * * * *